(12) United States Patent
Osypka (10) Patent No.: US 11,285,303 B2
(45) Date of Patent: Mar. 29, 2022

(54) BALLOON DILATION ASSEMBLY WITH AV NODE/HIS BUNDLE SENSING-STIMULATION SYSTEM

(71) Applicant: Peter Osypka Stiftung, Grenzach-Wyhlen (DE)

(72) Inventor: Peter Osypka, Grenzach-Wyhlen (DE)

(73) Assignee: Peter Osypka Stiftung, Grenzach-Wyhlen (DE)

( * ) Notice: Subject to any disclaimer, the term of this patent is extended or adjusted under 35 U.S.C. 154(b) by 475 days.

(21) Appl. No.: 16/406,222

(22) Filed: May 8, 2019

(65) Prior Publication Data
US 2019/0344056 A1 Nov. 14, 2019

(30) Foreign Application Priority Data
May 14, 2018 (EP) .................................. 18020205

(51) Int. Cl.
*A61M 25/10* (2013.01)
*A61B 18/14* (2006.01)
(Continued)

(52) U.S. Cl.
CPC ..... *A61M 25/1011* (2013.01); *A61B 18/1492* (2013.01); *A61M 25/1002* (2013.01);
(Continued)

(58) Field of Classification Search
CPC .......... A61M 25/1011; A61M 25/1002; A61M 25/1018; A61B 17/12136;
(Continued)

(56) References Cited

U.S. PATENT DOCUMENTS 6,245,064 B1 6/2001 Lesh et al.
6,315,733 B1 * 11/2001 Zimmon ............ A61B 5/02152
600/481
(Continued)

FOREIGN PATENT DOCUMENTS

CA 1305385 C 7/1992
DE 102012111984 A1 6/2014
(Continued)

OTHER PUBLICATIONS

European Search Report issued in EP18020205.3, dated Nov. 16, 2018.

*Primary Examiner* — Michael F Peffley
*Assistant Examiner* — Bo Ouyang
(74) *Attorney, Agent, or Firm* — Locke Lord LLP; Scott D. Wofsy (57) ABSTRACT

A balloon dilation assembly configured to be used for performing balloon valvuloplasty in order to dilate a stenotic heart valve, in particular a stenotic aortic valve.
The assembly comprises at least three outer balloons (12), (13), (14) evenly arranged in a circle around a central balloon (11) and fixed to the central balloon, and comprises a further outer balloon (15) which is shorter in length compared with balloons (11), (12), (13), (14) and which is not fixed to the central balloon, whereby each balloon has a separate filling tube (1), (2), (3), (4), (5) used for inflating each balloon separately, characterized in that the short outer balloon (15) is equipped with a sensing and/or stimulation system comprising an electrical pole (21).

9 Claims, 6 Drawing Sheets

(51) Int. Cl.
    *A61B 17/12*    (2006.01)
    *A61B 17/00*    (2006.01)
    *A61B 18/00*    (2006.01)

(52) U.S. Cl.
    CPC .................. *A61B 17/12136* (2013.01); *A61B 2017/00243* (2013.01); *A61B 2017/1205* (2013.01); *A61B 2018/0022* (2013.01); *A61B 2018/00577* (2013.01); *A61M 25/1018* (2013.01); *A61M 2210/125* (2013.01)

(58) Field of Classification Search
    CPC .. A61B 2017/00243; A61B 2017/1205; A61B 2210/125
    See application file for complete search history.

(56) References Cited

U.S. PATENT DOCUMENTS

| | | | | |
|---|---|---|---|---|
| 2012/0209375 | A1* | 8/2012 | Madrid | A61F 2/2427 623/2.11 |
| 2013/0150956 | A1 | 6/2013 | Yohanan et al. | |
| 2018/0133443 | A1 | 5/2018 | Osypka | |
| 2018/0344250 | A1* | 12/2018 | McKinney | A61B 5/6853 |

FOREIGN PATENT DOCUMENTS

| | | | |
|---|---|---|---|
| EP | 0231725 | A1 | 8/1987 |
| EP | 3320943 | A1 | 5/2018 |
| WO | 2009/100394 | A2 | 8/2009 |

\* cited by examiner

BALLOON DILATION ASSEMBLY WITH AV NODE/HIS BUNDLE SENSING-STIMULATION SYSTEM

CROSS REFERENCE TO RELATED APPLICATIONS

This Application claims the benefit of priority to European Patent Application No. EP 18020205.3 filed on May 14, 2018, the contents of which is incorporated herein by reference in its entirety.

The present disclosure relates to a balloon dilation assembly configured for performing balloon valvuloplasty in order to dilate a stenotic heart valve, in particular a stenotic aortic valve.

Transcatheter aortic valve implantation (TAVI) is a common treatment of aortic stenosis. In most cases the replacement valve is delivered transfemoral; a balloon catheter is placed in the femoral artery (in the groin) and guided into the heart.

The replacement valve can also be delivered transapical through the wall of the heart. In this procedure mini-thoracotomy is performed to obtain a straight access to the left ventricular apex. Sutures are firstly placed to close afterwards the thoracotomy opening. The left ventricle apex is punctured with a standard access needle. A guide wire is inserted into the left ventricle and directed through the aortic valve and to the ascending aorta. Then a trocar is inserted into the left ventricular apex to maintain intraventricular access. The balloon catheter is then guided via the guide wire through the left ventricle to the aortic valve. Aortic balloon valvuloplasty is performed during a brief episode of rapid ventricular pacing. A compressed heart valve is delivered through the trocar and positioned across the aortic annulus. Once in position, the balloon is inflated to secure the valve in place.

The inflated balloon blocks the blood flow. To overcome this problem the European patent publication EP0231725 corresponding to the Canadian patent publication CA1305385 suggests a dilation device having three balloons arranged around a support tube. Upon inflation of the balloons flow channels (so called flow tubes) are formed between the balloons through which blood can flow.

US patent publication 20130150956 discloses a balloon assembly that can be used to expand prosthetic valve having a central balloon and peripheral balloons surrounding the center balloon. The peripheral balloons include a first set of balloons and a second set of relatively shorter balloons.

During balloon valvuloplasty dilating forces are generated not only within the aortic valve itself but also within the surrounding tissue where the atrioventricular (AV) node/HIS bundle lie. The AV node/HIS bundle are part of the electrical conduction system of the heart.

The pressure applied to the AV node/HIS bundle upon inflation of the balloons may disturb the conduction of the electric signals of the sinus node via AV node/HIS bundle into the ventricles so that a block may occur in the electrical conduction system (AV block). In case of an AV block the patient needs a pacemaker after the replacement of the heart valve.

In order to minimize tissue damage in the area of the AV node/HIS bundle it is known to use particularly shaped balloons. The balloon assembly of e.g. the German Patent Publication DE10 2012 111 984 has three circularly cylindrical areas with different diameters, whereby the diameter of the second area is smaller than the diameter of the first and third area.

The European patent publication EP3320943 (published May 16, 2018) describes a balloon dilation assembly comprising a central balloon and at least three outer balloons. One of the outer balloons must be shorter in length compared to the remaining outer balloon to avoid any pressure to the AV node/HIS bundle area. It might be difficult to insert said assembly so that the outer balloons do not press the AV node/HIS bundle area.

The object of the present invention is to minimize the pressure applied to the AV node/HIS bundle area during balloon valvuloplasty or even to avoid any pressure to the AV node/HIS bundle area. A further object of the invention is to locate the AV node/HIS bundle area in order to reach pressure-free fit of the balloons.

The present invention is a technological improvement of the device described in EP3320943 corresponding to US20180133443.

The above mentioned object of the invention is achieved by a balloon dilation assembly comprising at least three outer balloons evenly arranged in a circle around a central balloon and a further outer balloon which is shorter in length compared to the three outer balloons and the central balloon. The short outer balloon functions as "sensing balloon" and is equipped with an AV node/HIS bundle sensing and/or stimulation system comprising an electrical pole (pacing pole) connected to a cardiac signal monitor and/or stimulator. The electrode pole is placed at the outer balloon skin. Each outer balloon (except the "sensing balloon") is fixed to the central balloon. The "sensing balloon" with the pole is not fixed to the central balloon and is movable out of the delivery sheath to its sensing position. The sensing position is reached when the pole receives a signal or when the pole generates an appropriate signal. Then the "sensing balloon" is moved out of the critical AV node/HIS bundle area to its final position.

In a further embodiment, one of the outer balloons is replaced by two balloons arranged one after the other. The distance between said two balloons may be fixed or may be independently movable. The distally placed first balloon lies in use position in the area of the heart valve and is used—like all other outer balloons—to dilate the heart valve. The proximally placed second balloon is used to stabilize the alignment of the balloon catheter assembly. The distally placed first balloon and the proximally placed second balloon are shorter in length compared to the remaining outer balloons and the central balloon. The distally placed first balloon and the proximally placed second balloon each have a separate filling tube which is movable into each other. By moving the two balloons either together or relative to each other along the longitudinal axis the balloons can be shifted. The electrical pole is placed at the outer skin of the proximally placed second balloon. This proximal placed second balloon thus functions as "sensing balloon".

In another arrangement an insulated coil with a blanc space in the middle acting as electrical pole runs along the distally placed first balloon and the proximally placed second balloon facing the AV node/HIS bundle area.

Each balloon has a separate filling tube used for inflating each balloon separately with a liquid or a gas. Due to the individual filling of each balloon, the pressure in each balloon can vary. The "sensing balloon" with the pole is rather weakly inflated, certainly not inflated to full pressure and is configured to contact the area of the AV node/HIS bundle without pressure in order to monitor a sensing signal of the AV node/HIS bundle or to generate a stimulation signal to the AV node/HIS bundle.

The outer balloons are evenly arranged in a circle around the central balloon. There are flow channels between each pair of two adjacent outer balloons through which blood can flow. The outer balloons (except the sensing balloon) may have the same length as the central balloon or may be shorter. They preferably have the same length as the central balloon.

When the assembly is in use position the central balloon and the outer balloons are positioned in the area of the heart valve. The short "sensing balloon" lies proximal to the heart valve next to the area of the AV node/HIS bundle and an electrical signal is received or generated guaranteeing perfect pressure-free fit of the assembly in the AV node/HIS bundle area. The assembly is then inflated to dilate the aortic valve.

The balloons of the assembly are made as known valvuloplasty balloons. Length, diameter and wall thickness of the balloons may vary.

The number of balloons being present can vary to match the anatomy of the heart valve. A minimum number of three outer balloons being evenly arranged around the central balloon should be present for ensuring an even dilation of the stenotic heart valve. A number of 3 to 6 balloons are well feasible.

The central balloon is guided via the firstly placed guide wire to the aortic valve area.

In one embodiment the balloon dilation assembly further consists of a protective element in form of a filter or of an occluder. The protective element is fixed to the guidewire at its upper end and is inserted together with the guidewire to the aortic arch. The protective element is helpful to catch atherosclerotic plaques during the valve replacement process. The protective element is preferably a self-expandable braiding filter made of shape memory material, e.g. made of nitinol.

The assembly according to the invention is suitable for performing balloon valvuloplasty using the transfemoral approach as well as using the transapical approach.

Using the transfemoral approach the steps are:
inserting a guidewire through a patient's vasculature and pulling the guidewire through the valve to be dilated;
advancing the balloon dilation assembly—as described above—over the guide wire to the valve to be dilated;
rotating the balloon assembly until the sensing pole of the "sensing balloon" receives an appropriate signal;
monitoring the AV node/HIS bundle signal or generating a stimulation signal;
inflating the balloons by introducing an inflation medium through the filling tubes and dilating the heart valve;
deflating the balloons by removing the inflation medium; and
removing the balloon dilation assembly from the patient's body.

Using the transapical approach comprising the steps are:
inserting a guidewire into the heart through a puncture in the myocardium and pressing the guidewire through the valve to be dilated up to the aortic arch and position the filter;
inserting a delivery sheath with a pre-inserted balloon dilation assembly—as described above—over the guidewire and advancing an valvuloplasty balloon catheter to the valve to be dilated;
optionally rotating the balloon assembly until the sensing pole of the "sensing balloon" receives an appropriate signal;
monitoring the AV node/HIS bundle signal or generating a stimulation signal by means of the electrode pole placed at the "sensing balloon";
inflating the balloons by introducing an inflation medium through the filling tubes and dilating the heart valve;
deflating the balloons by removing the inflation medium; and
removing the balloon dilation assembly from the patient's body;
removing the guide wire with the filter.

The transapical approach is preferred. Due to the short distance between the myocardium entrance and the aortic valve it is easier to place the "sensing balloon" and thus the whole assembly in the right position.

DETAILED DESCRIPTION OF THE FIGURES

The following figures show the inventive balloon dilation assembly in more detail.

Figure 1:
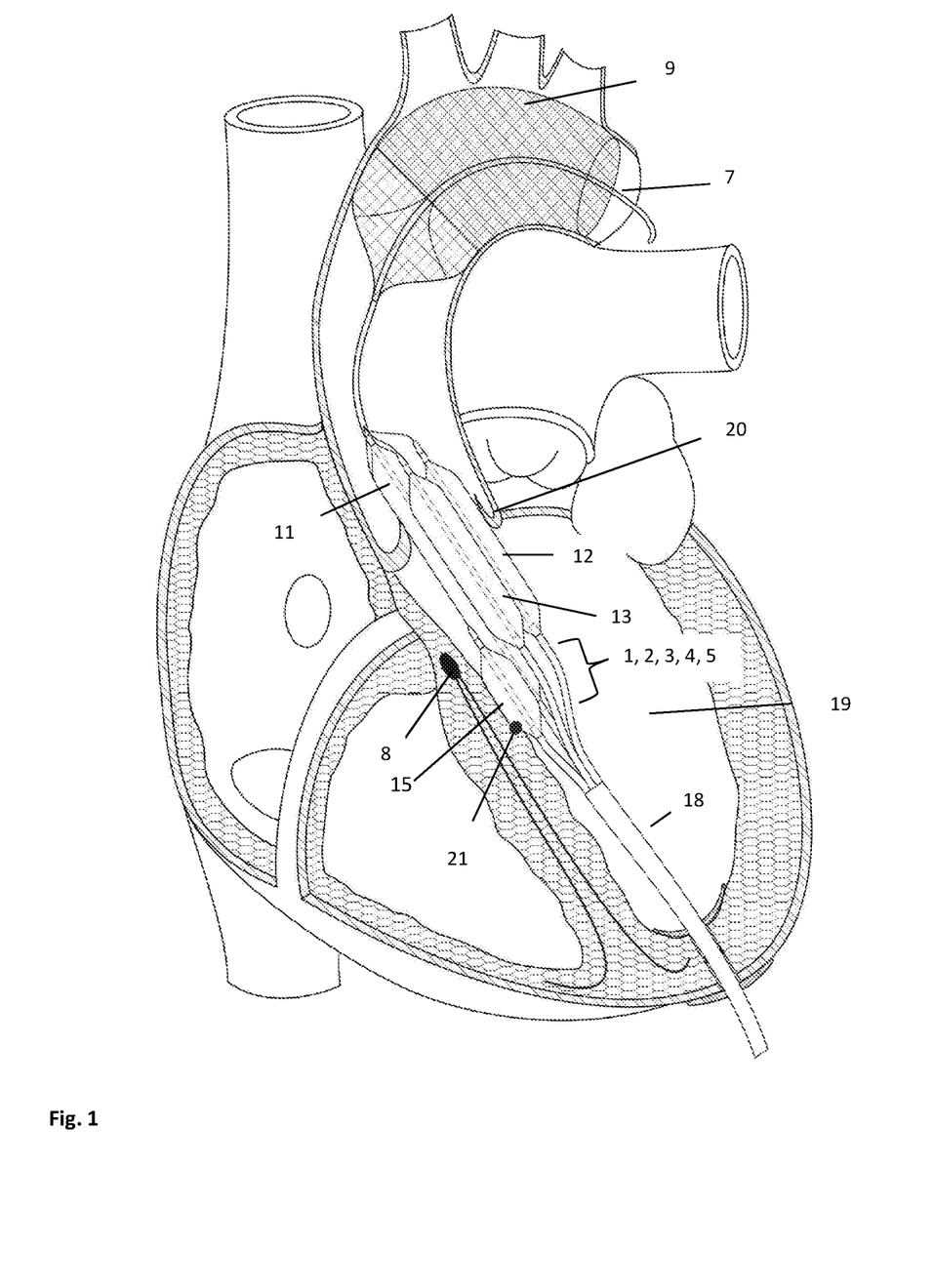

The reference signs are as follows:
1 filling tube of the central balloon
2, 3, 4, 5, filling tubes of the outer balloons
6 flow channel
7 guide wire
8 AV node/HIS bundle
9 self-expandable filter
11. central balloon
12, 13, 14 outer balloons
15 short outer balloon "sensing balloon"
16 distally placed outer balloon
17 proximally placed outer balloon ("sensing balloon")
18 delivery sheath
19 left ventricle
20 aortic valve
21 sensing and/or stimulation pole
22 RF-ablation pole
AV Atrioventricular node
HIS HIS bundle FIG. 1 illustrates a schematic view of the heart with the balloon dilatation assembly according to the invention being placed. The assembly is used in a transapical approach of performing aortic balloon valvuloplasty. Using guide wire (7) the balloon dilation assembly has been guided through the left ventricle (19), fed to the aortic valve (20) and further to the aortic arch. FIG. 1 shows the assembly with inflated balloons.

The AV node/HIS bundle (8) is marked with a black dot with left and right branches. The AV node/HIS bundle is located in the heart septum beneath the aortic valve.

The central balloon (11) and the three outer balloons (12, 13, 14) which are evenly arranged around the central balloon are placed in the area of the aortic valve (20) and are configured to dilate the aortic valve. The outer balloon (14) is only seen in the cross sectional view of FIG. 2.

The outer balloon (15) is shorter in length compared to the outer balloons (12, 13 and 14).

The outer balloon (15) carries an electrode pole (21) at the outer balloon skin. The electrical lead to the cardiac monitoring device and/or stimulation device is guided inside the filling tube or outside along the filling tube of the "sensing balloon" (15). The electrical lead to the monitor is not shown in the drawing. Balloon (15) with pole (21) functions as "sensing balloon". Each balloon can be separately filled with a liquid or a gas via its filling tube (1, 2, 3, 4, 5) and is thus inflated. Due to the individual filling of each balloon, the pressure in each balloon can vary. The "sensing balloon" with the pole is rather weakly inflated, certainly not inflated to full pressure and is configured to contact the area of the AV node/HIS bundle without any pressure in order to monitor a sensing signal of the AV node/HIS bundle or to generate a stimulation signal of the AV node/HIS bundle. If a sensing signal is received, the dilation assembly is correctly placed. Due to the short distance between the myocardium entrance and the aortic valve it is easy to place the "sensing balloon" and thus the whole assembly in the right position.

When the sensing is completed balloon (15) is moved out of the critical AV node/His bundle area.

The filling tubes (1, 2, 3, 4, 5) are coming out of the delivery sheath (18). Through the filling tube to the central balloon the guide wire (7) is drawn. Each outer balloon (12, 13, 14) is fixed to the central balloon (11). The "sensing balloon" (15) is not fixed and is thus movable. The balloon dilatation assembly is placed using guide wire (7). Flow channel run lengthwise along the balloons between each pair of two adjacent balloons.

A self-expandable braided filter (9) made of nitinol is shown in its expanded configuration. The braiding is placed in the upper part of the guide wire (7) in the area of the aortic arch and is helpful to catch atherosclerotic plaques during the balloon valvuloplasty procedure.

Figure 2:
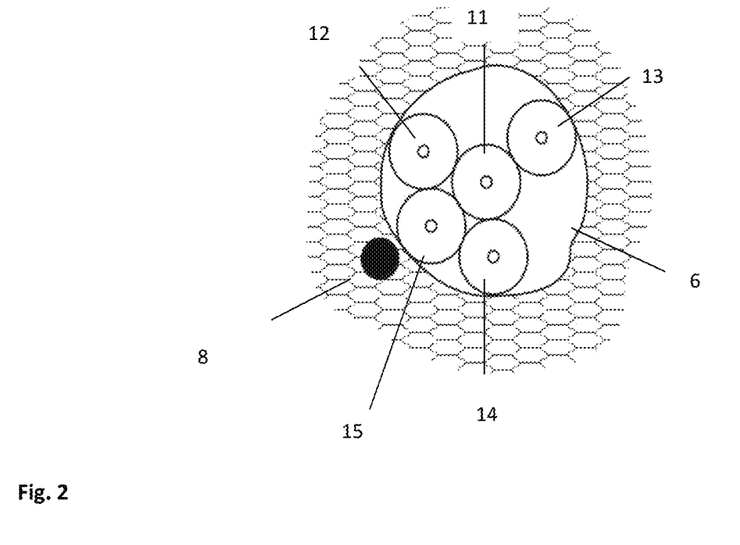

FIG. 2 is a cross sectional view of the inserted assembly as shown in FIG. 1. The outer balloons (12, 13, 14) are arranged symmetrically in a circle around the central balloon (11). Flow channels (6) are generated between each pair of two adjacent outer balloons. The short outer balloon (15) which is the "sensing balloon" lies next to the AV node/HIS bundle (8).

Figure 3:
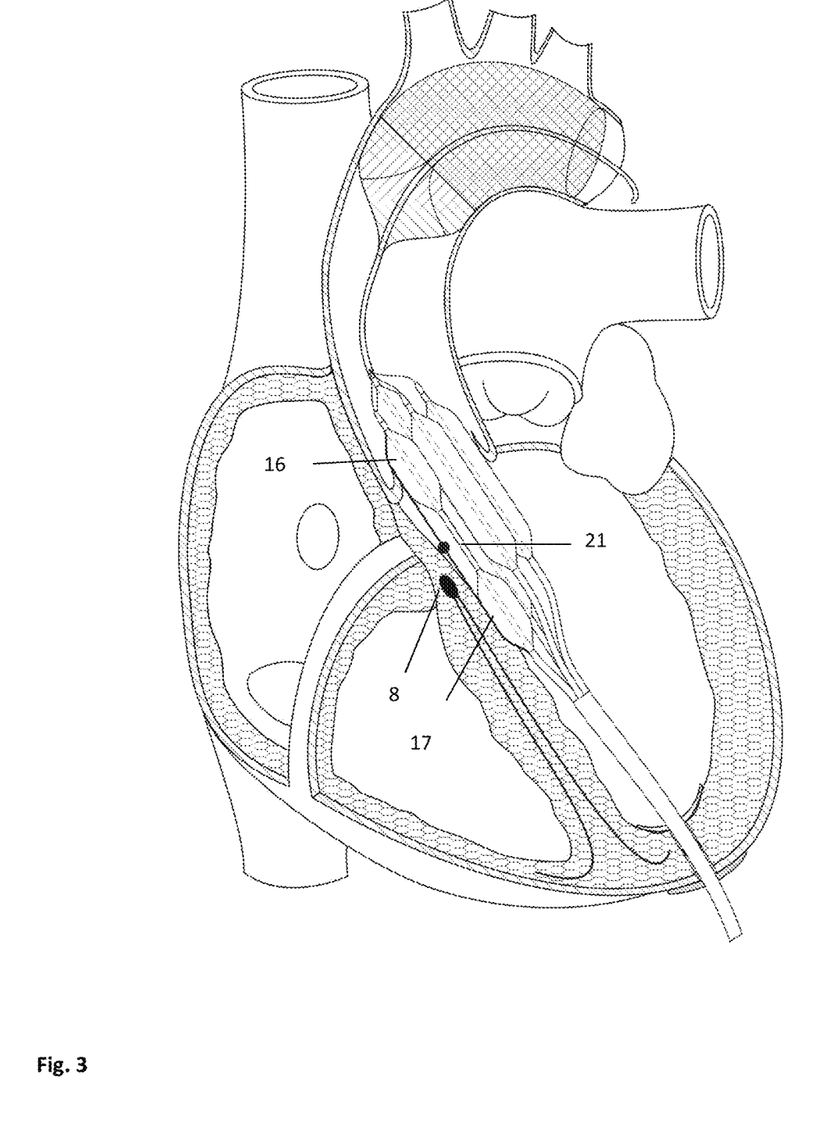

FIG. 3 illustrates a schematic view of the heart as FIG. 1 does. The reference signs of FIG. 1 are not repeated in the drawing of FIG. 3 to avoid a confusingly large number of signs. A balloon dilatation assembly as shown in FIG. 1 has been inserted. In contrast to the balloon dilation assembly illustrated in FIG. 1 one of the outer balloons consists of two balloons arranged one after the other. Balloon (16) is distally placed; balloon (17) is proximally placed. Balloon (16) is used to dilate the aortic valve like the other outer balloons. Balloon (16) and balloon (17) each have separate filling tubes which are movable into each other. An insulated coil with a blanc space in the middle acts as electrical pole (21). The insulated coil runs along balloon (16) and (17) facing to the AV node/HIS bundle area (8). Thus, balloon (17) functions via pole (21) as "sensing balloon". Balloon (16) and (17) are not fixed to the central balloon (11). Moving balloon (16) and (17) allows to move pole (21) in order to reach the correct sensing position.

Figure 4:
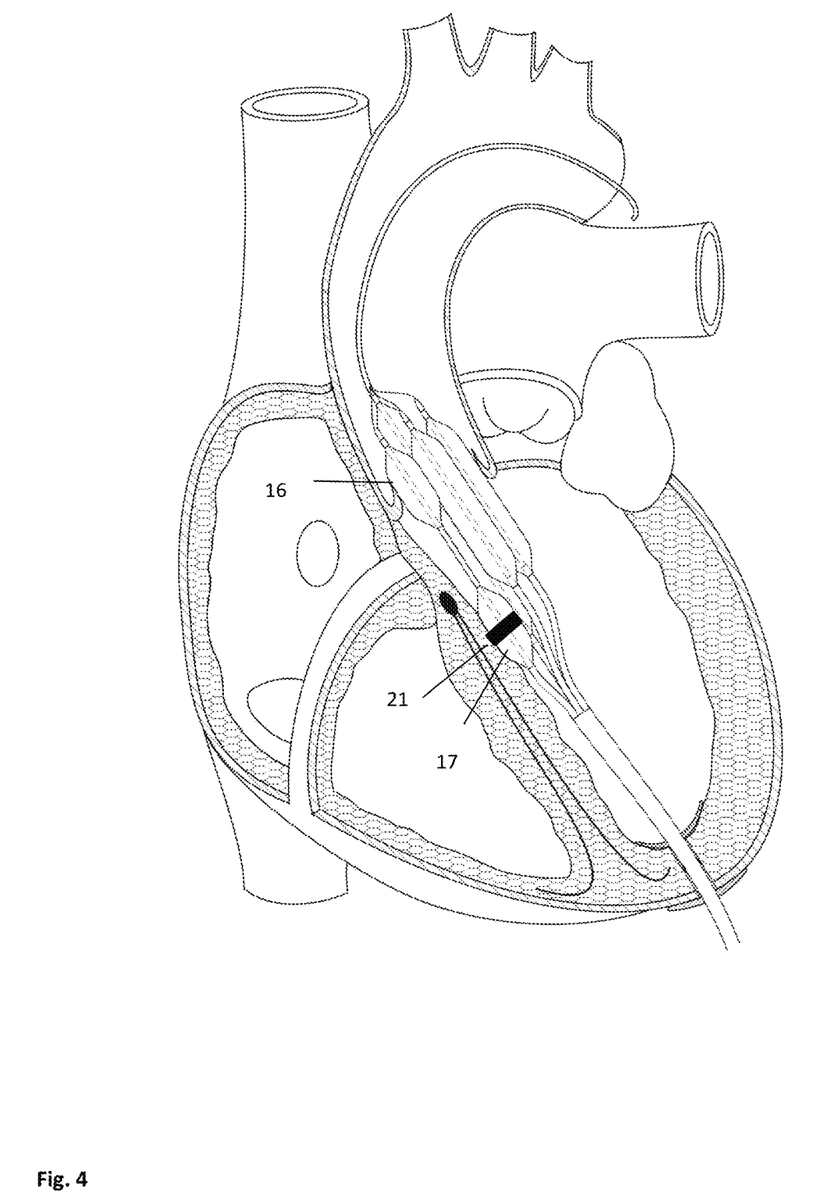

FIG. 4 corresponds to an assembly shown in FIG. 3. Balloon (17) carries pole (21) and functions as "sensing balloon". Pole (21) may be in form of a coated electrical conductive material ring.

Figure 5:
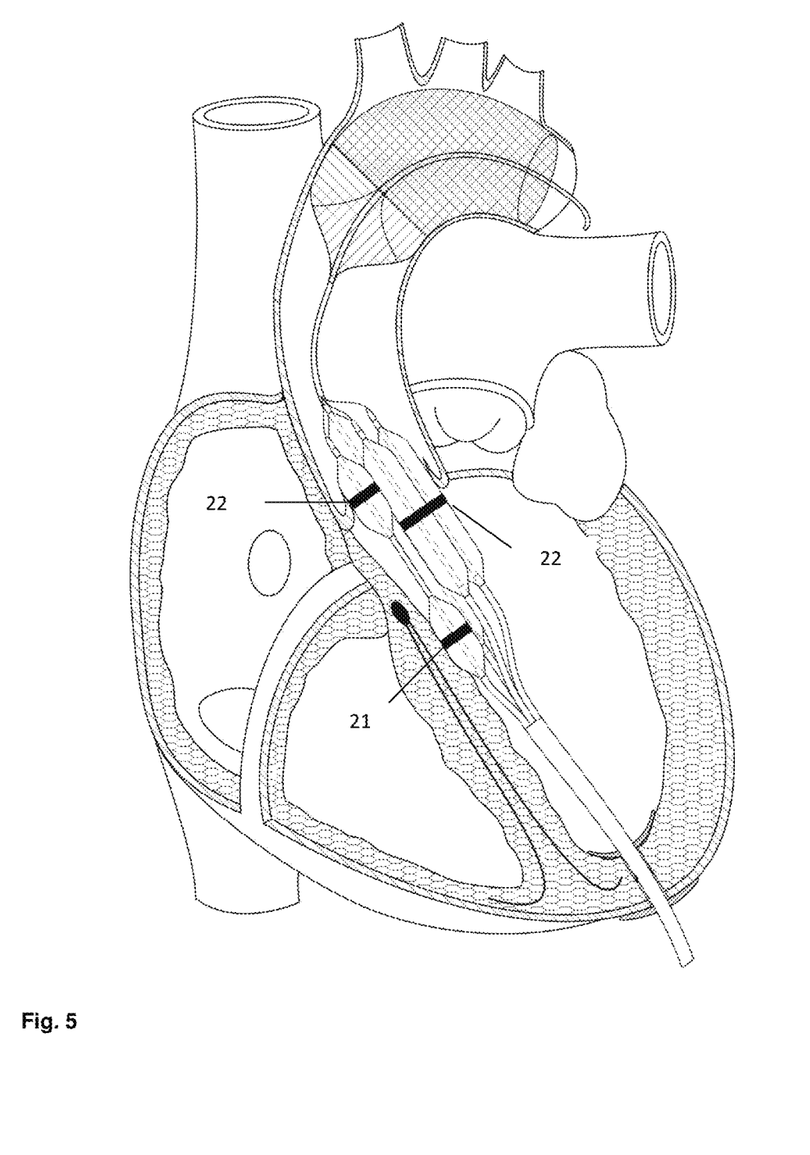

FIG. 5 corresponds to an assembly shown in FIG. 4. In contrary to the assembly described in FIG. 4 further poles (22) may be used for RF ablation of the heart valve area.

Figure 6:
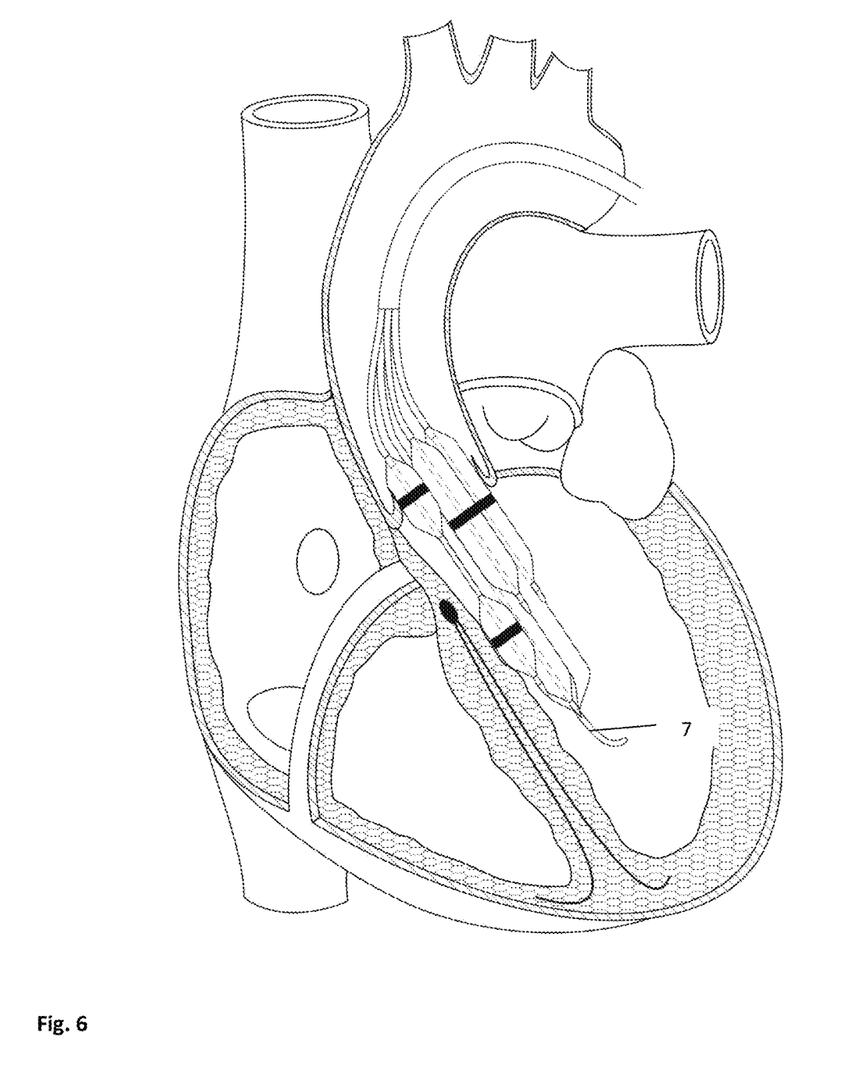

FIG. 6 illustrates a schematic view of the heart with the balloon dilatation assembly according to FIG. 5 being placed in a transfemoral approach of performing aortic balloon valvuloplasty. Using guide wire (7) the assembly has been guided through the femoral artery, fed to the aortic valve and further to the left ventricle.

The invention claimed is:

1. A balloon dilation assembly configured to be used in balloon valvuloplasty comprising:
at least three outer balloons evenly arranged in a circle around a central balloon and fixed to the central balloon, and including a further outer balloon which is shorter in length compared with the at least three outer balloons and which is not fixed to the central balloon, whereby each balloon has a separate filling tube used for inflating each balloon separately, wherein the shorter outer balloon is equipped with a sensing and/or stimulation system that includes an electrical pole.

2. The balloon dilation assembly according to claim 1, having three to six outer balloons.

3. The balloon dilation assembly according to claim 1, wherein the at least three outer balloons have the same length.

4. The balloon dilation assembly according to claim 1, wherein one of the outer balloons is an arrangement of two balloons arranged one after the other and having separate filling tubes which are movable into each other, whereby the proximal one of the two arranged balloons carries the electrode pole.

5. The balloon dilation assembly according to claim 4, wherein the two arranged balloons are movable together or relative to each other.

6. The balloon dilation assembly according to claim 1, wherein one of the outer balloons is an arrangement of two balloons arranged one after the other and having separate filling tubes which are movable into each other, and the assembly further comprises an insulated coil with a blanc space in its middle acting as pole, the coil running along the two arranged balloons.

7. The balloon dilation assembly according to claim 6, wherein the two arranged balloons are movable together or relative to each other.

8. The balloon dilation assembly according to claim 1, further comprising at least one RF ablation pole.

9. The balloon dilation assembly according to claim 1, further having a protective element in form of a filter or an occluder, placed in the area of the aortic arch in a use position.

* * * * *